(12) United States Patent
Palmer

(10) Patent No.: US 7,555,931 B2
(45) Date of Patent: Jul. 7, 2009

(54) NON-DESTRUCTIVE TESTING OF THE LINING OF A PROCESS VESSEL

(75) Inventor: Greg Palmer, Coorparoo (AU)

(73) Assignee: P-Response IP Pty Ltd, Coorparoo (AU)

( * ) Notice: Subject to any disclaimer, the term of this patent is extended or adjusted under 35 U.S.C. 154(b) by 0 days.

(21) Appl. No.: 11/879,430

(22) Filed: Jul. 17, 2007

(65) Prior Publication Data

US 2008/0060412 A1    Mar. 13, 2008

Related U.S. Application Data

(63) Continuation-in-part of application No. PCT/AU2006/000021, filed on Jan. 10, 2006.

(30) Foreign Application Priority Data

Jan. 17, 2005    (AU) .............................. 2005900171

(51) Int. Cl.
*G01M 7/00* (2006.01)

(52) U.S. Cl. ..................................... 73/12.09

(58) Field of Classification Search ...... 73/12.01–12.14
See application file for complete search history.

(56) References Cited

U.S. PATENT DOCUMENTS

| | | | | |
|---|---|---|---|---|
| 4,479,386 A * | 10/1984 | Beggs et al. | ................... | 73/582 |
| 4,502,329 A * | 3/1985 | Fukunaga et al. | .............. | 73/573 |
| 4,872,345 A * | 10/1989 | Dicks | .......................... | 73/597 |
| 5,117,835 A * | 6/1992 | Mick | .......................... | 600/561 |
| 5,242,512 A * | 9/1993 | Bagley et al. | ................ | 148/558 |
| 5,983,701 A | 11/1999 | Hassani et al. | | |
| 6,782,732 B2 * | 8/2004 | Huang et al. | ................ | 73/12.07 |
| 2006/0186585 A1* | 8/2006 | Sadri | ............................ | 266/78 |

FOREIGN PATENT DOCUMENTS

| GB | 2 326 235 A | 12/1998 |
|---|---|---|
| JP | 2001-249117 | 9/2001 |
| JP | 2003-043021 | 2/2003 |

\* cited by examiner

*Primary Examiner*—Max Noori
(74) *Attorney, Agent, or Firm*—Greer, Burns & Crain, Ltd.

(57) ABSTRACT

A process for the non-destructive testing of a refractory lined process vessel including the steps of: (a) striking an external wall of a process vessel internally lined with a refractory material with an impulse hammer; (b) measuring selected frequency characteristics of the refractory lined process vessel; and (c) analysing the measured frequency characteristics and determining the integrity of the internal lining of refractory material from the measured frequency characteristics.

32 Claims, 12 Drawing Sheets

- ▨ MISSING "HOT FACE"
- ▩ UNSTABLE REFRACTORY
- ▧ STABLE REFRACTORY

FFT of cyclone roof showing high mobility over the range 0 to 0·2 kHz indicating a very thin plate (or refractory)

FFT trace of the repaired cyclone roof showing very low average mobility indicating very stiff and well bonded refractory layers.

☒ MISSING "HOT FACE"

☐ UNSTABLE REFRACTORY

☒ STABLE REFRACTORY

NON-DESTRUCTIVE TESTING OF THE LINING OF A PROCESS VESSEL

CROSS-REFERENCE

This application is a continuation-in-part of PCT International Application No. PCT/AU2006/000021, filed 10 Jan. 2006, which claims priority from Australian Patent Application No. 2005900171 filed 17 Jan. 2005.

FIELD OF THE INVENTION

The present invention relates to the testing of the integrity of the lining of a process vessel. In particular, the present invention relates to a process for the non-destructive testing of the (refractory) lining of a process vessel.

BACKGROUND OF THE INVENTION

Process vessels lined with refractory concrete, bricks and other ceramic materials are used in a number of applications including in the cement, petroleum, petro-chemicals, mineral processing, alumina and other industries. From time to time the linings break down and need to be replaced or repaired. Failure in the lining of a process vessel includes de-bonding of the refractory layers, failure of anchor supports, delamination, voiding, cracking or honeycombing in the refractory layers, and the like.

In order to maintain process vessels that are lined with refractory materials, it is generally necessary for the process vessels to be taken offline and the refractory lining to be inspected. Taking a process vessel offline for the inspection of refractory linings when the refractory lining is in good order is unnecessary and may result in loss of productivity. Certain process vessels may take many hours, or even days, to cool sufficiently or to be in a condition for inspection. The inspection of the refractory lining is also a potentially hazardous operation. Operators enter a process vessel in order to inspect and determine the condition of the lining. Incidents have occurred where linings have fallen from a process vessel while an operator has been inside the vessel.

In addition to visual inspection from inside the process vessel, a variety of destructive tests may be used to determine the integrity of the refractory lining. For example, core drilling has been used in order to assess the integrity of the refractory lining. Destructive testing is not generally desirable as the testing itself can compromise the integrity of the lining.

BRIEF DESCRIPTION OF THE INVENTION

We have now found a process for the non-destructing testing of a refractory lined process vessel that overcomes or ameliorates at least one of the problems described above or provides the user with a useful or commercial choice. The testing can be carried out from outside the vessel, but can be used inside the vessel also.

In accordance with a first embodiment of the present invention there is provided a process for the non-destructive testing of a refractory lined process vessel comprising the steps of:

(a) striking an external wall of a process vessel internally lined with a refractory material with an impulse hammer;

(b) measuring selected frequency characteristics of the refractory lined process vessel; and (c) analysing the measured frequency characteristics and determining the integrity of the internal lining of refractory material from said measured frequency characteristics.

Suitably, the selected frequency characteristics may include vibration amplitude.

Advantageously, the process of the present invention enables the testing of the integrity of an internal lining of a refractory material of a refractory lined process vessel whilst the vessel is online or before entry of maintenance personnel into the process vessel. This permits the more efficient remediation of the lining of refractory material by avoiding the need for periodic maintenance and enabling the vessel to be taken offline for maintenance only when required. In addition, the down time, the period whilst the vessel is offline, may be reduced due to the ability to better plan the remediation of the lining of refractory material due to the determination of the integrity of the internal lining prior to taking the vessel offline. The hazards associated with the entry by operators into the process vessel may advantageously be reduced by identifying those sections of refractory material susceptible for catastrophic failure and falling from the shell of the process vessel. By being able to assess the lining of refractory material whilst the vessel is online or offline, it is also possible to conduct remediation of the refractory lining prior to deterioration to the point where such a catastrophic failure is likely.

In the process of the present invention, the external wall of the process vessel is struck with an impulse hammer. The impulse hammer used in the present invention is required to apply an impact to the external wall of the process vessel and to measure the force of said impact. The hammer provides an impulse that consists of a nearly constant force applied over a broad frequency range. Typically, the frequency range over which the force is applied, will be determined by the tip of the hammer. Generally impulse hammers are provided with a variety of tips that are capable of generating frequencies up to 2000 Hz. The applied force is generally measured with an integral quartz force transducer (or load cell) mounted on the striking end of the hammer. The transducer converts the impact force applied into an electrical signal.

It is preferred that the impulse hammer used in the present invention is a modally tuned impulse hammer, that is an impulse hammer that is designed to eliminate bouncing (multiple impacts). The impulse hammer for use in the present invention may also include inter-changeable softer and stiffer hammer tips to provide the desired frequency response in the process vessel. In addition, extenders can be used to increase or decrease the hammer mass, thereby increasing or decreasing the duration of impact and providing an increased or decreased energy in the low frequency range of the signal imparted by the impact.

The response of the vessel to the impact may be measured by one ore more accelerometers, such as geophones. The accelerometers measure the response of the process vessel across a range of frequencies and provides measured data for selected frequency characteristics of the refractory lined process vessel.

Typically, the accelerometer is a geophone having a single degree of freedom where the output of the geophone is generated by a coil moving through a magnetic field. The voltage in the coil being directly proportional to the relative velocity between the coil and the magnetic field.

The output from the accelerometer and the force transducer of the impulse hammer are analysed across the frequency range for a variety of frequency characteristics in order to determine the integrity of the internal lining of refractory material.

Process vessels lined with refractory materials typically comprise an outer shell. The outer shell is generally formed from steel or other convenient materials. Attached to the outer shell is the refractory lining. A variety of refractory linings are employed to insulate the process vessel, but for the sake of convenience, the present invention will be described with respect to a refractory lining comprising insulating layer(s) and a dense "hot face" layer. It will be appreciated that refractory linings of other configurations will be used in a variety of the applications for which the present invention is applicable.

In a refractory lining comprising an insulating layer and a dense "hot face" layer the refractory materials are typically held in place by anchors attached to the shell. Anchors, normally formed of stainless steel or a steel alloy, are welded to the interior surface of the vessel shell and an insulation layer is affixed to the inner surface of the shell by the anchor. More recently, ceramic anchors have been employed. A dense "hot face" layer is also affixed using the anchors and retained in abutment with the insulation layer. The insulation layer and the dense hot face layer are typically formed from a plurality of bricks or other segments for ease of construction or maintenance.

Failure of the refractory lining may result from the removal of one or both of the layers of the refractory lining, delamination between the respective layers of refractory linings, delamination between the refractory lining and the shell of the vessel, voids forming in the respective layers of the refractory lining, cracking or other failures of the refractory lining and the like.

Refractory linings are typically formed from ceramic materials and accordingly are relatively brittle (at temperatures less than 1000° C.) and subject to brittle failure resulting in potentially catastrophic failure by the refractory lining being completely removed from the inner surface of the shell of the process vessel.

The frequency characteristics of the refractory lined process vessel selected for determining the integrity of the internal lining of refractory material may be selected from the group consisting of dynamic stiffness, average mobility, slope of average mobility, peak frequency/ies, peak to average mobility ratio and combinations thereof.

The mobility, measured in m/sec/N, of the refractory lined pressure vessel is determined by the velocity of the response, such as may be measured by an accelerometer or velocity transducer, divided by the force applied by the impulse hammer such as may be measured by the force transducer. The determination of mobility is calculated for each selected frequency point. Selected frequency points may be at predetermined frequency intervals. The instruments used to determine mobility may be calibrated in order to verify the accuracy of the measured parameters.

The dynamic stiffness of the refractory lined process vessel is obtained from the mobility slope in the low frequency range. Typically, dynamic stiffness is determined from the mobility slope between 0 and 200 Hz, although lower ranges such as 0 to 50 Hz may also be used. The slope or decay of the force frequency curve may be used to obtain the stiffness of the structure at the test point.

The dynamic stiffness slope or the force decay slope allows the determination of the refractory quality, indicative refractory thickness and/or the support conditions for the refractory material. The slope portion of the mobility plot or the modal frequency in the range from 0 to 200 Hz defines the dynamic stiffness of the lining of refractory material around the test point. The dynamic stiffness is determined from the inverse of the compliance, where the compliance is the slope of the mobility plot in the low frequency range. The modal frequency is determined from the mobility frequency plot.

The average mobility is typically determined across a higher frequency range, such as from 100 to 1500 Hz or alternatively 100 to 800 Hz.

The average mobility is related to the density and thickness of the refractory lining around the test point. The average mobility of a known sound (intact) area of the vessel is compared with other areas on the vessel. A steady mobility (relatively constant value) over the selected frequency range generally is indicative of a solid section in the lining. A reduction in plate thickness or debonding at an interface corresponds to an increase in average mobility or the mobility at a modal frequency. For example, when total de-bonding of a layer of the refractory material occurs or cracking then the refractory lining becomes more mobile. The average mobility or mobility at a modal frequency increases reflecting the thickness of the upper de-bonded layer. In addition, honeycombing in the refractory layers will reduce the dampening and hence the average mobility will increase with increasing frequency.

The peak mobility or peak to average mobility ratio is related to de-bonding or delamination of the refractory material. Where there is a loss of support of the refractory lining such as between the shell of the process vessel or between respective layers of refractory material, an increase in average mobility and a decrease in the modal frequency is observed.

Without wishing to be bound by theory, it is believed that when the stress wave is generated at the surface with the impulse hammer, a bending moment is formed which generates a vibration in the structure. The vibration of the structure at the test location is dependent on the shape, thickness and type of materials used. Examples of structural configurations that lead to a mechanical impedance and or vibration include a change in material, a change in cross sectional area and other forms of discontinuity.

When the bending moment encounters the impedance change, the vibration at that point/area and can be recorded by the accelerometer.

DETAILED DESCRIPTION OF THE DRAWINGS

The present invention will now be described with reference to the accompanying drawings and examples that serve to illustrate the present invention and are not intended to limit the scope of the invention disclosed.

Figure 1:
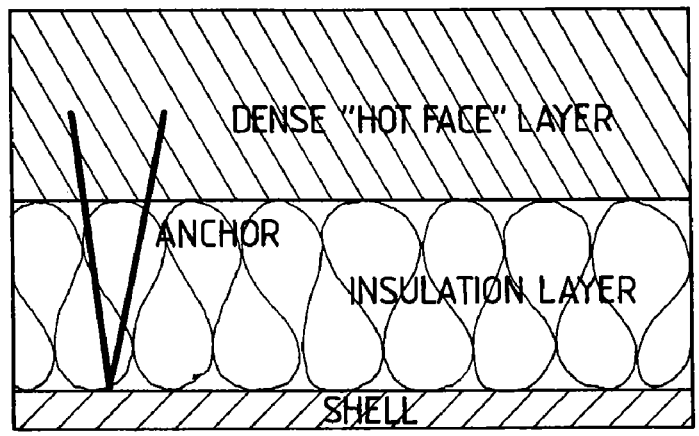
FIG. 1 shows a typical configuration of the lining of a process vessel.

FIG. 1 shows a typical configuration of the lining of a process vessel. The vessel has an outer shell with anchors attached thereto. An insulation layer is attached to the shell by the anchors and a dense hot face layer is affixed to the insulation layer, also by the anchors.

Figure 2:
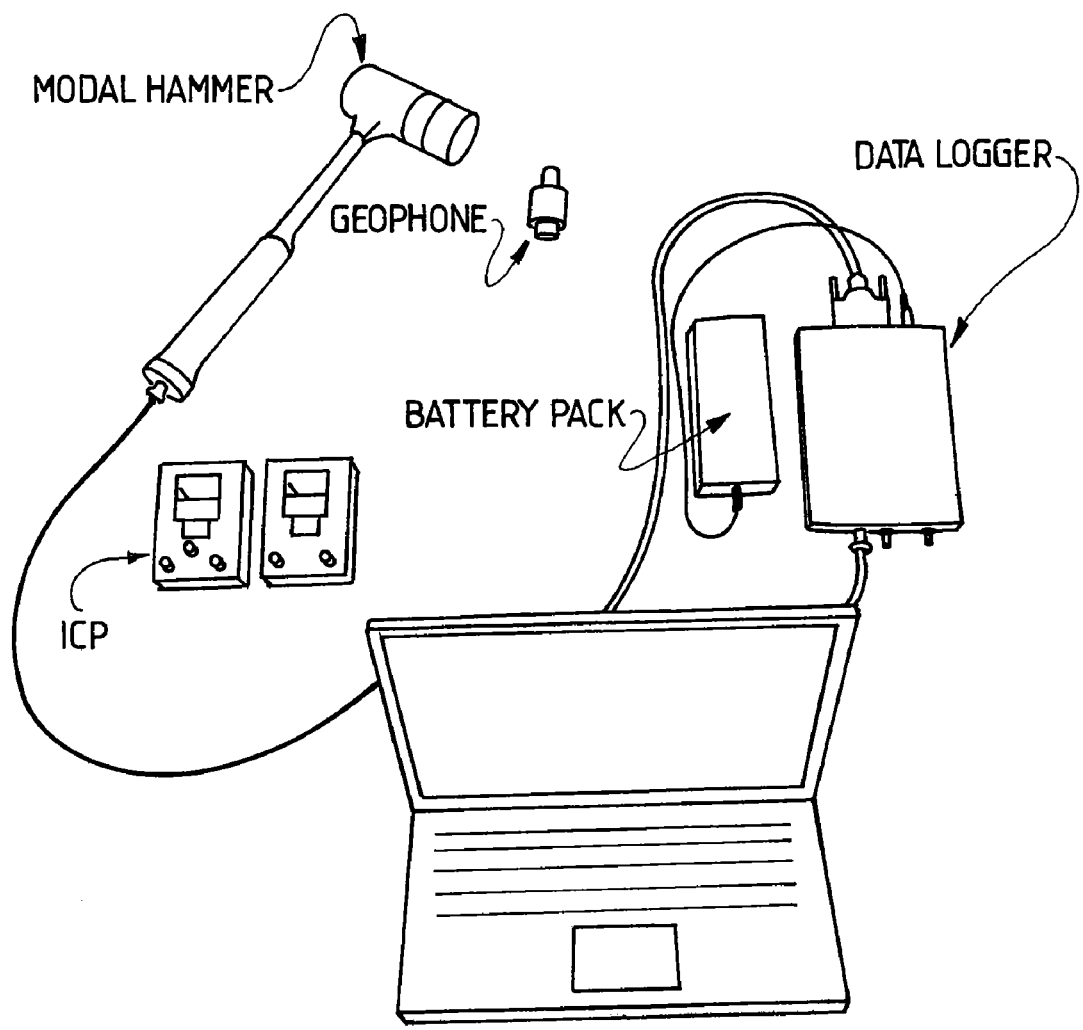
FIG. 2 shows the equipment used for the non-destructive testing of the lining of the process vessel in accordance with an embodiment of the present invention.

FIG. 2 shows the equipment used for the non-destructive testing of the lining of the process vessel. The equipment includes a modal hammer which is connected to an ICP power supply (without gain) and the output from the ICP is connected to channel A of a data logger. A geophone is connected to an ICP (with gain) and the gain is typically set to a factor of times ten but can be 1 or 100. The output from this ICP is connected to channel B of the data logger. A parallel cable is connected from the data logger to a laptop computer to enable the data to be processed.

Figure 3:
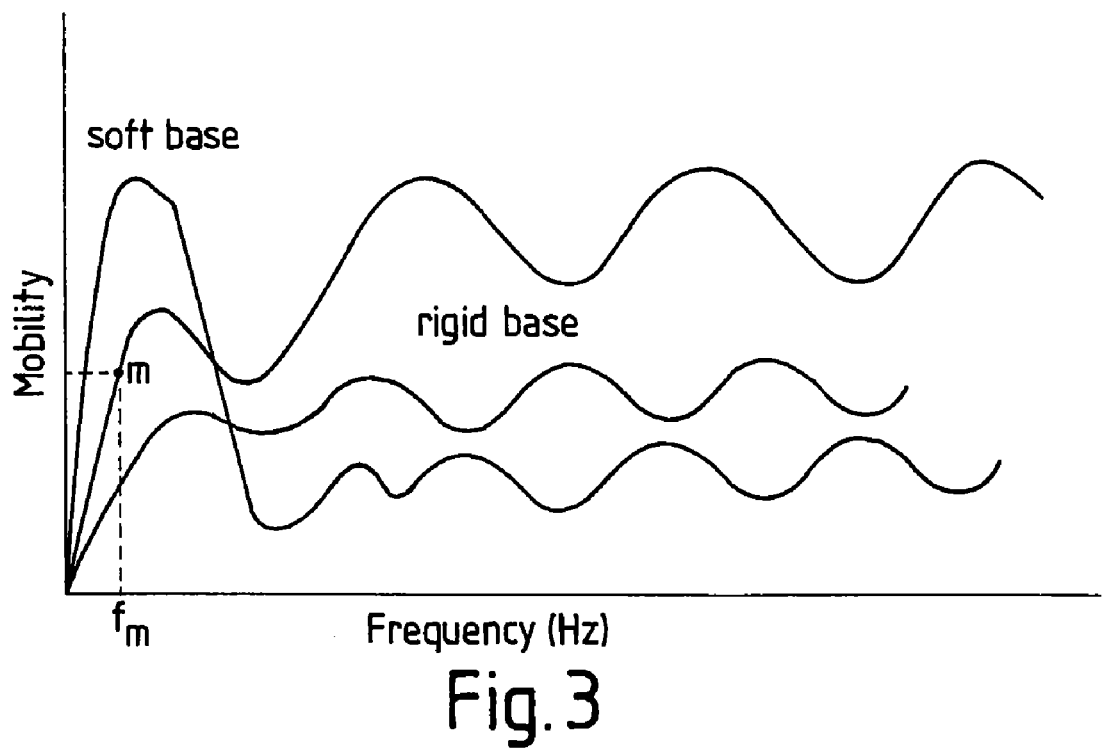
FIG. 3 shows an idealized mobility plot showing variations in material stiffness.

FIG. 3 shows an idealized mobility plot showing variations in material stiffness.

Figure 4:
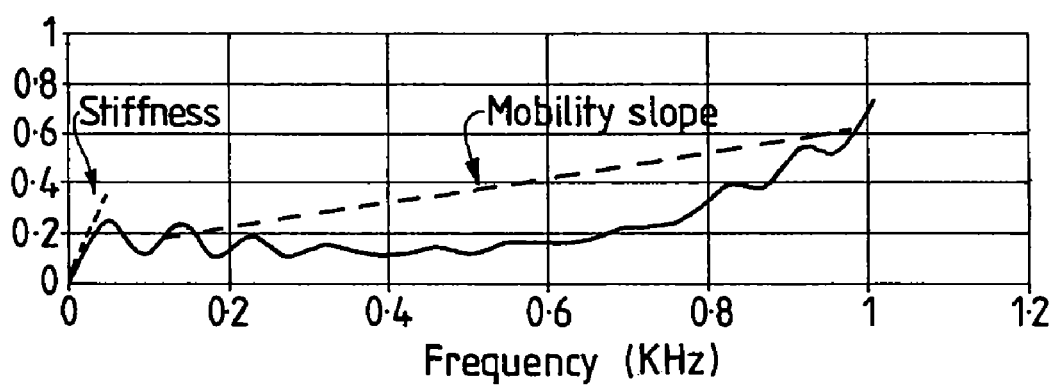
FIG. 4 shows the determination of dynamic stiffness and the mobility slope.

FIG. 4 shows the determination of dynamic stiffness and the mobility slope. The dynamic stiffness is determined in MN/mm from a mobility slope in the frequency range of from 0 to 50 Hz. An average mobility from 100 to 800 Hz is a measure of the element thickness and concrete quality. The slope of average mobility over the range of from 100 to 1000 Hz shows the degree of concrete consolidation and the proximity of structural shape changes. The peak mobility at a low frequency and/or the peak to average mobility ratio shows the support beneath slabs, thickness of a refractory lining and/or, voiding.

Figure 5:
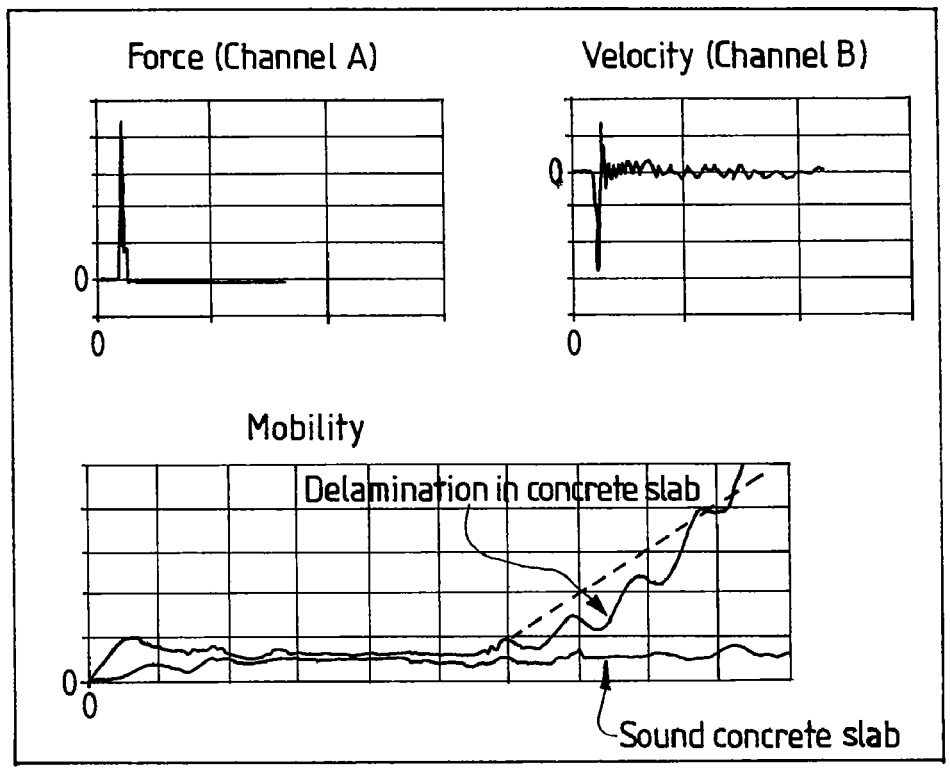
FIG. 5 shows a typical response in concrete in which (fine) delamination of the concrete slab has occurred.

FIG. 5 shows a typical response in concrete in which honeycomb or decreased density at that point in the concrete slab has occurred.

Figure 6:
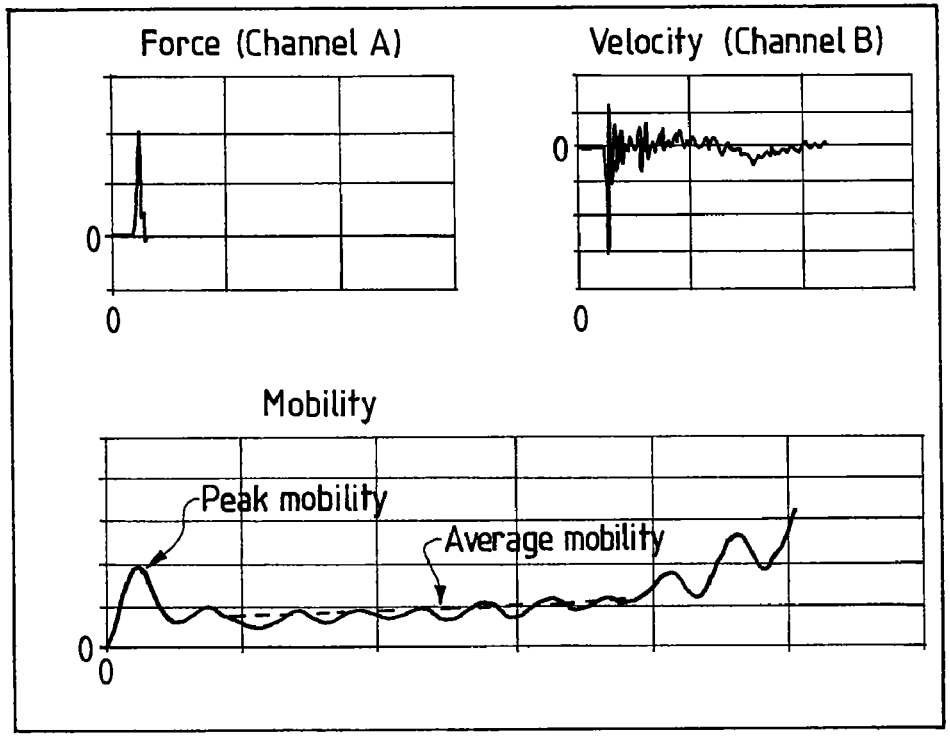
FIG. 6 shows the measurement of peak to mean mobility ratio that indicates the presence and degree of either de-bonding or voids.

FIG. 6 shows the measurement peak mobility and/or peak to mean mobility ratio that indicates the presence and degree of either de-bonding or voids.

Figure 7:
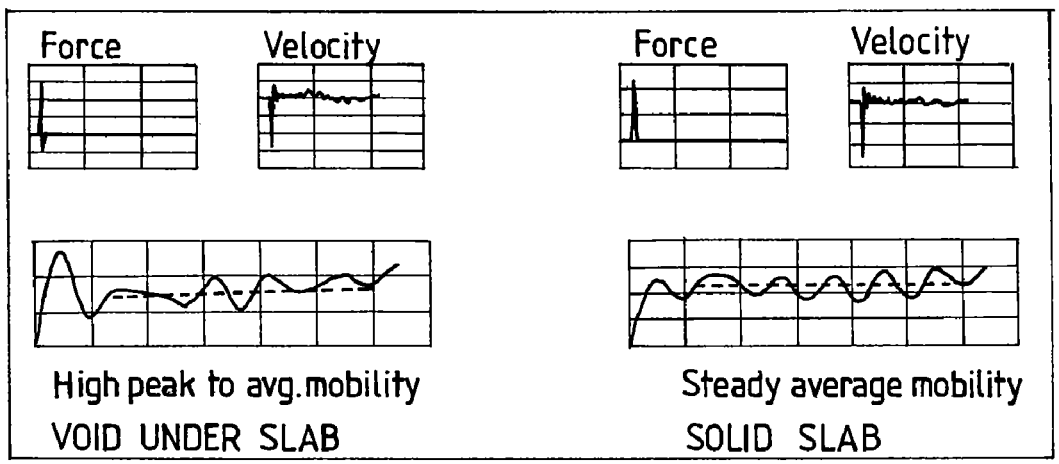
FIG. 7 shows a comparison in which concrete with a void under the slab is indicated by the presence of a high peak to average mobility.

FIG. 7 shows a comparison in which concrete with a void under the slab is indicated by the presence of a high peak to average mobility or high peak at low frequency.

Figure 8:
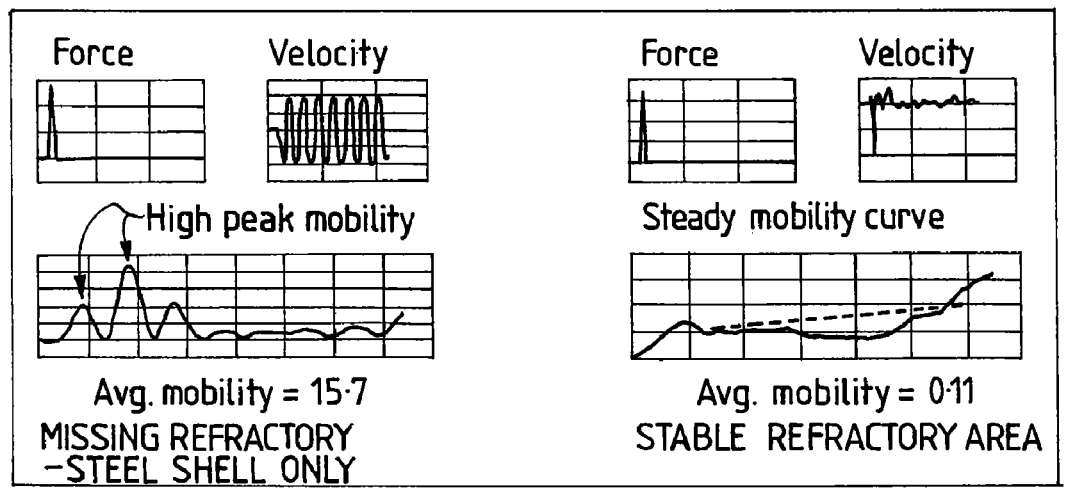
FIG. 8 shows the response of a section of the lining in which the refractory lining is missing.

FIG. 8 shows the response of a section of the lining in which the refractory lining is missing. It can be seen that the difference in average mobility is significant.

Figure 9:
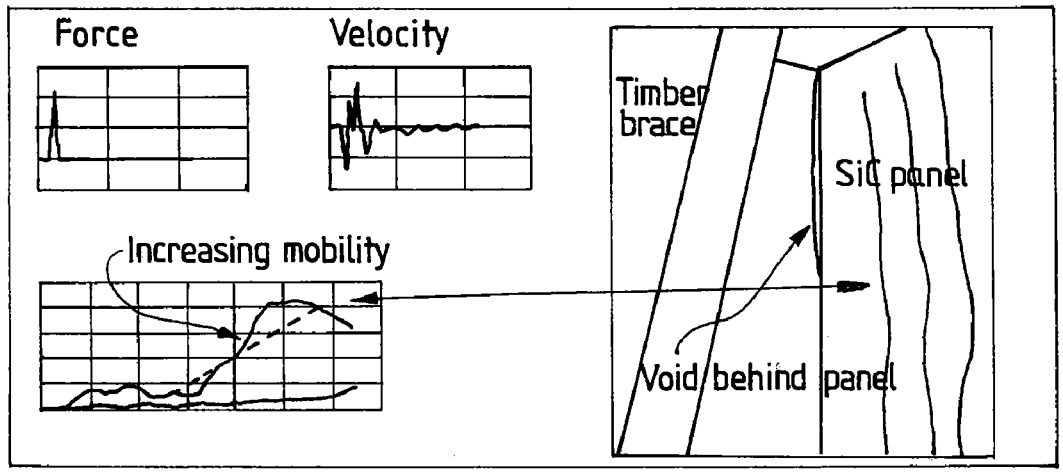
FIG. 9 is a typical response from a vertical refractory lined duct showing mobility for a lining that includes a void.

FIG. 9 is a typical response from a vertical refractory lined duct showing mobility for a lining that includes a void.

Figure 10:
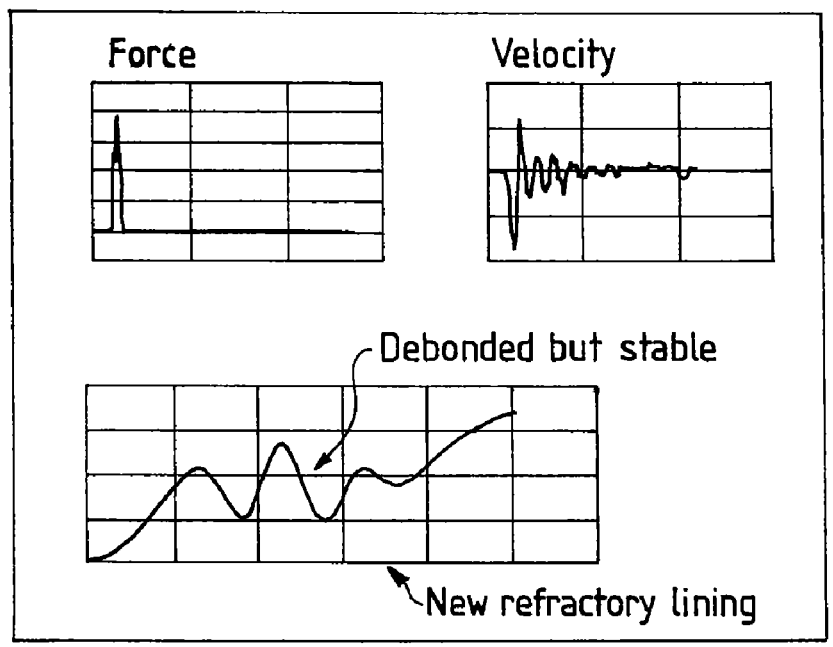
FIG. 10 shows a typical response for a refractory lined duct with both a new lining and a de-bonded lining.

FIG. 10 shows a typical response for a refractory lined duct with both a new lining and a de-bonded lining.

At a plant trial, the refractory lining of a vessel in a cement plant was assessed in which it was found that a section of hot faced lining was missing, a section of lining was sound and the remaining areas of lining were present but not sound.

Figure 11:
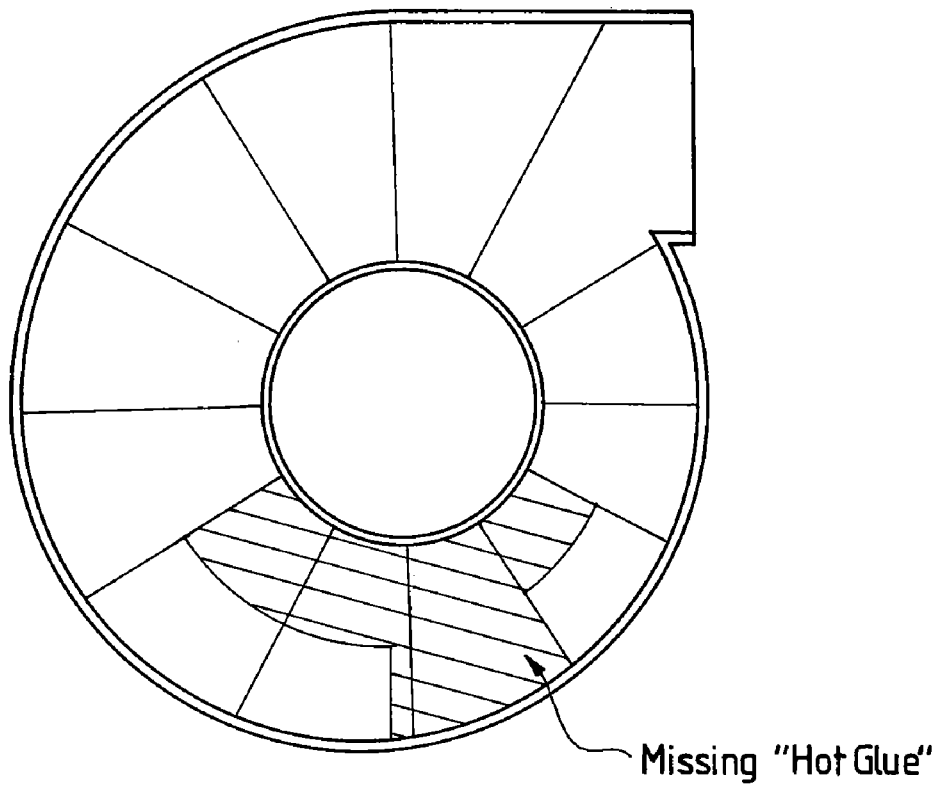
FIG. 11 shows a map of the tested cyclone roof showing the location of test points and damaged areas.

FIG. 11 shows a map of the tested cyclone roof showing the location of test points and damaged areas.

Figure 12:
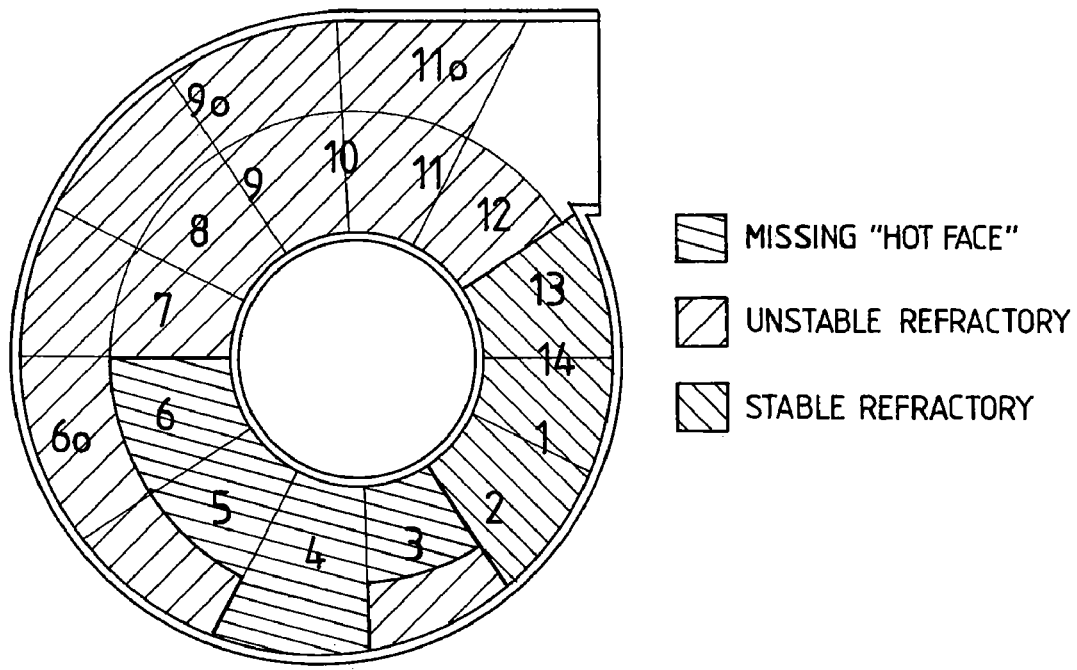
FIG. 12 shows a graphical representation of the cyclone roof showing good and bad areas.

FIG. 12 shows a graphical representation of the cyclone roof showing good and bad areas.

A mobility response curve which is generally flat indicates a solid structure (see points, 4on1 roof12n13. An increasing average mobility indicates the refractory is thin or debonded (see Table I points 2 and 3).

TABLE I

Cyclone 4 on 1 roof results

| Point | Average mobility m/s/N × $10^{-5}$ (as new) | peak mobility/ average mobility m/s/N × $10^{-5}$ | | Debond frequency Hz | Visual inspection |
| --- | --- | --- | --- | --- | --- |
| 1 | 0.142 | 1.1 | 0.64 | 69 | Solid but anchors broken |
| 1 and 2 | | 1.8 | 3.02 | 69 | Small void behind "hot face" |
| 2 | 0.23 | 1.3 | 1.42 | 69 | Small void behind "hot face" |
| 2 and 3 | | 1.1 | 0.88 | 92 | Solid but anchors broken, debonded at the interface |
| 3 | 0.156 | 1.5 | 1.9 | 92 | Small void behind "hot face" |
| 4 | 0.141 | 10 | 3.7 | 137 | Inner "hot face" layer missing |
| 4 outer | 0.125 | | | | |
| 5 | 0.143 | 10.3 | 3.2 | 115 | Inner "hot face" layer missing |
| 5 outer | 0.098 | | | | |

TABLE I-continued

Cyclone 4 on 1 roof results

| Point | Average mobility m/s/N × $10^{-5}$ (as new) | peak mobility/average mobility m/s/N × $10^{-5}$ | | Debond frequency Hz | Visual inspection |
|---|---|---|---|---|---|
| 6 | 0.159 | 10.1 | 2.53 | 115 | "hot face" visually dropped |
| 6 outer | 0.111 | | | | |
| 7 | 0.118 | 8.7 | 2.3 | 137 | Large void behind "hot face" |
| 7 outer | 0.122 | | | | |
| 8 | 0.125 | 17 | 2.82 | 92 | Large void behind "hot face" |
| 8 outer | 0.09 | | | | |
| 9 | 0.263 | 14 | 3.78 | 92 | Large void behind "hot face" |
| 9 outer | 0.126 | | | | |
| 10 | | 3.02 | 1.78 | 69 | Void behind "hot face" |
| 11 | 0.08 | 9.4 | 3.37 | 115 | Large void behind "hot face" |
| 11 outer | 0.133 | | | | |
| 12 | 0.124 | 0.32 | 0.556 | 160 | Solid but slight debonding at the interface |
| 12 and 13 | | 0.818 | 0.693 | 115 | Solid but slight debonding at the interface |
| 13 | 0.114 | 0.67 | 1.02 | 69 | Solid but anchors corroded |
| 14 | 0.129 | | | | |

Table I shows the average mobility for a vessel, in this case a cyclone roof before and after repair.

The average mobility was measured over the range of 0.1 to 0.4 kHz (but could be across the range 0 to 1 kHz). The upper limit of the average mobility range was limited to the fact that the force frequency starts to approach zero near 0.7 kHz. Extending the average mobility range above 0.7 kHz can lead to serious error in the results.

In a preferred embodiment the process of the present invention uses a low-strain impact to send stress waves through and flex the tested element. The element flexes in both compression and shear and a velocity transducer placed adjacent to the impact point, receives this vibration. An element's response to the impact-generated elastic wave will be damped by the plate's intrinsic rigidity, also known as body damping.

The time trace of both the hammer force and the velocity transducer are processed into frequency using the Fast Fourier Transform (FFT) algorithm. The velocity spectrum is normalized by the force. The parameter is termed "mobility". Variation in mobility of a composite plate is based on the fact that materials of different densities and thicknesses have different mobilities.

Without wishing to be bound by theory, our research has shown that thick solid plates have very low mobility values <1×$10^{-5}$ m/s/N. Plates which are thin or damaged will have a high or very high mobility value, >1×$10^{-7}$ m/s/N. When there are a number of broken anchors at the interface between layers then the mobility at that point will increase.

The assessment of a vessel requires a general understanding of the lining construction, ie thickness, density, anchoring. Test points are marked out in a grid pattern where possible, each point is labelled and the location recorded. A vessel may be stiffened externally with steel beams but testing is done in the open areas.

Each point is tested by impacting the surface with the modal hammer and the vibration is recorded by the geophone. The voltage signals are captured by the high speed datalogger and converted to both velocity and force. The number of data points obtained is maximized by adjusting the datalogger sample number and duration.

In some embodiments in accordance with the present invention, testing measures the mobility, and hence the integrity of an area, between the impact hammer point and the geophones. For one geophone point there can be two or more results, impacting around of the geophone. It is possible for the signals to vary as the impact location is moved because the testing area changes. For example, on one side of the geophone, the lining may be very rigid (low mobility) with no cracks or loss in lining thickness. However, on the other side of the geophone, the lining may be more flexible (high mobility) as a result of the loss in lining thickness or cracks.

With refractory lined vessels which are constructed with outer steel shells it has been found by testing that the shell may separate in places where no anchors are present. When this occurs then the mobility at that point may increase (ie typically a point between anchors). To overcome this problem, where localized mobility may increase, yet the overall integrity of the structure is still sound, two geophones are used simultaneously. The geophones are positioned at a set distance of approximately 100 mm to 700 mm and the impact point is set at a distance of approximately 100 to 300 mm from a single geophone or at the centre between two geophones. The position of the geophones is set to lie between anchors or adjacent to an anchor. In this manner the overall integrity of the structure may be evaluated.

The process of the present invention involves a comparative test for the evaluation of concrete structures and refractory lined vessels, i.e. a known good point is compared to other points in the grid being evaluated or an "as new" condition signal is compared to the results of areas with a similar structure type, i.e. lining thickness, density, slab size.

The parameters used in the evaluation of the vessel structure we have used in this embodiment are listed below:

Mobility or average mobility from 100-600 Hz (function of element thickness and concrete layer stiffness) however the upper frequency range can vary up to 2000 Hz depending on the impact frequency Debond mobility is the peak mobility between 0-200 Hz. This indicates the degree of support beneath the steel shell, voiding or delamination.

The frequency curves are also used in the evaluation. If the same impact tip is used then the rapid decay of the force frequency such that the frequency approaches zero near 600 Hz, is indicative of a soft surface. A shift in the velocity frequency maximum peak to a lower value is indicative of a more flexible plate.

Comparing the Mobility

The average mobility value in the range of 100 up to 1500 Hz is directly related to the density and the thickness of a plate. A reduction in plate thickness corresponds to an increase in mean mobility. For example, when total debonding of an upper layer is present in a slab, ie the steel shell, then the mobility is very high, typically $>>50\times10^{-7}$ m/s/N. Any honeycombing in concrete or refractory layers will reduce the damping and hence the mobility over the tested frequency range will tend to increase in value.

We have found from testing, that an insulation material below the shell with a very low density <500 kg/m$^3$, will increase the mobility to values varying from $\sim 1\times 10^{-6}$ to $\sim 1\times 10^{-5}$ m/s/N.

It has also been found that the mobility value is directly related to the density and the thickness of a plate. A reduction in plate thickness corresponds to an increase in mean (or average) mobility. Any honeycombing in concrete or refractory layers will reduce the damping and hence the mobility over the tested frequency range will tend to increase in value. While cracking will increase the mobility of the low frequency mobility modes.

Debond Mobility

When debonding or delamination between the steel shell and the concrete or between the different concrete layers (eg insulation and "hotface" layers) is present there is loss of support beneath a concrete slab or the shell. The response behaviour of the uppermost layer (steel shell) controls the impulse response result. The debond mobility is the peak mobility below 200 Hz. When the debond mobility is greater than the average mobility then it can be concluded that the shell or the "hotface" at that point has separated from the refractory concrete and the impact point or velocity measurement point is not adjacent to an anchor.

Shift in Velocity Frequency Peaks

We have found from research that a shift in the velocity spectrum peak can occur due to the structure flexibility. In this case the average mobility can remain the same but there is a shift in the peak frequency or frequencies. The lower the main frequency peak then the greater the structure flexibility (ie the thinner the concrete lining).

Therefore from this parameter it is possible to determine the relative structure flexibility, i.e. damage.

If the same impact tip is used then the rapid decay of the force frequency such that the frequency approaches zero near 600 Hz (but could be >600 Hz) is indicative of soft surface or honeycomb or low density material being present. A shift in the velocity frequency maximum peak to a lower value is indicative of a more flexible or damaged lining.

Figure 13:
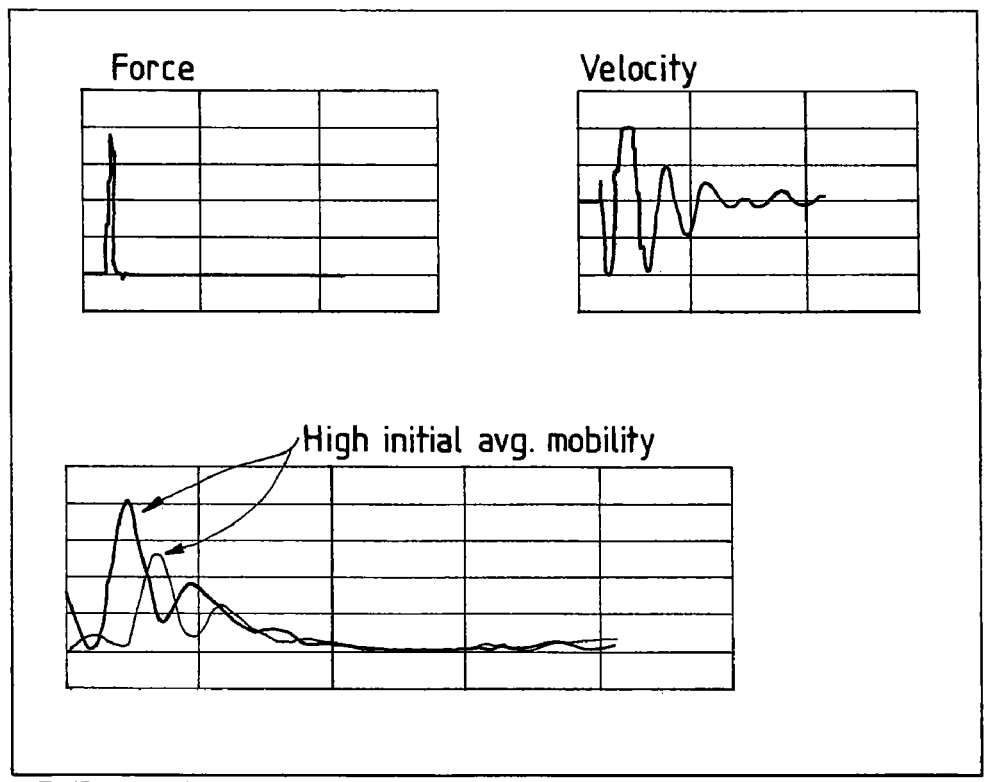
FIG. 13 shows a computer output and mobility curve (lower curve) for a very thin section of a cyclone roof.

FIG. 13 shows the P-Response computer output and mobility curve (lower curve) for a very thin section of the cyclone roof. The mobility in the range 0 to 200 Hz has peak mobility/ies indicating a very thin section like a steel plate or thin refractory concrete.

Figure 14:
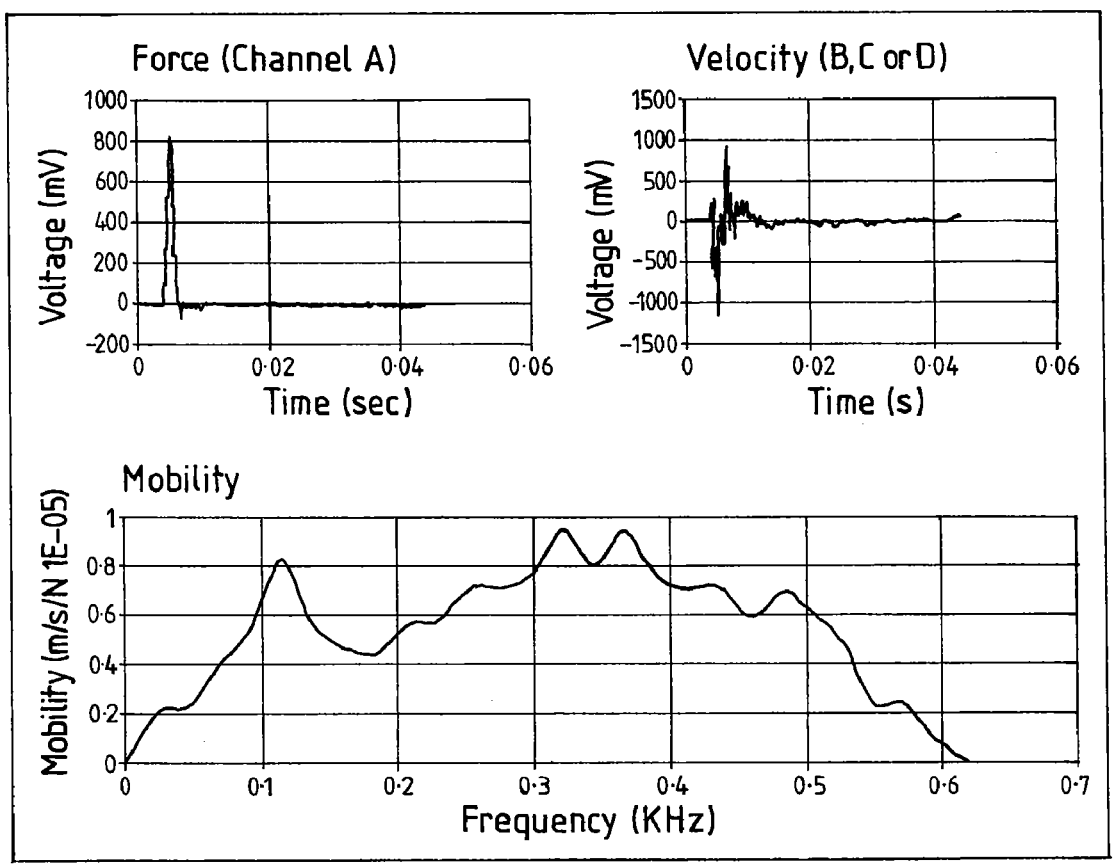
FIG. 14 shows the computer output and mobility curve (lower curve) for section of the cyclone with refractory present but debonded at the interface (ie the refractory anchors were broken)

FIG. 14 shows the P-Response computer output and mobility curve for section of the cyclone with refractory present but debonded at the interface. The average mobility for this curve has a max (y axis) value of $\sim 1.0\times 10^{-5}$ m/s/N.

Figure 15:
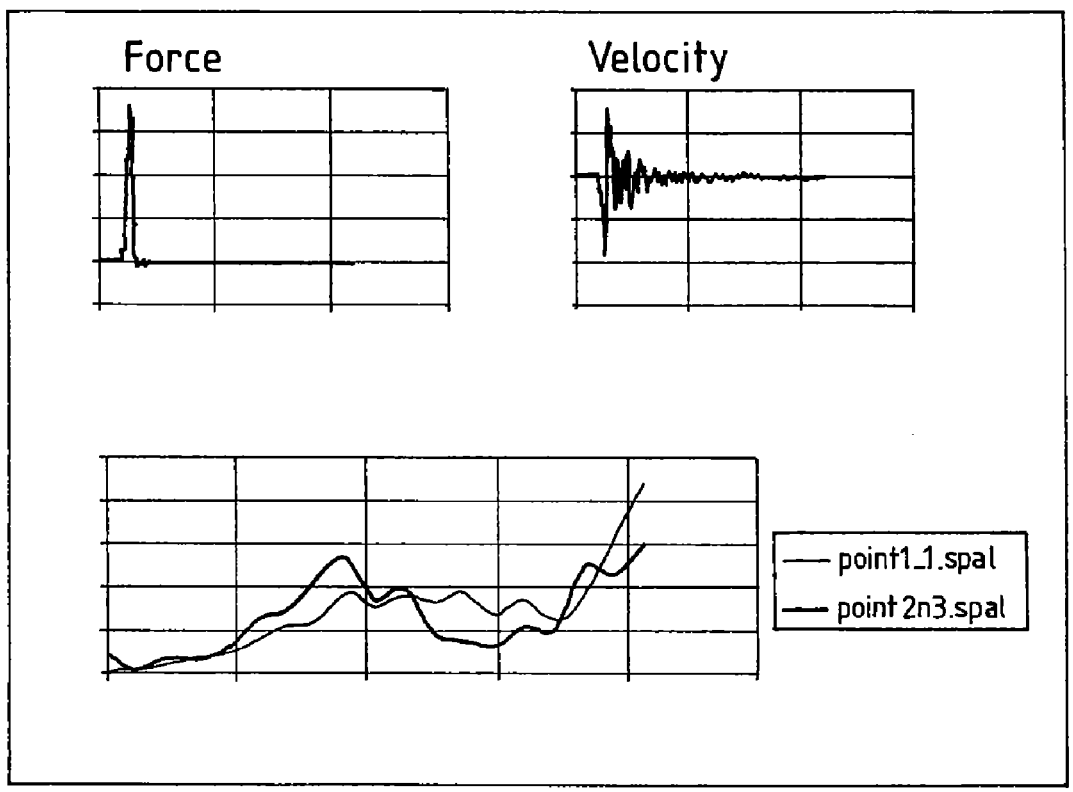
FIG. 15 shows the mobility response for the repaired cyclone roof.

FIG. 15 shows the mobility response for the repaired cyclone roof. The average mobility is very low in comparison to the damaged roof and the mobility curve is relatively flat (values above 0.7 kHz have been ignored).

Figure 16:
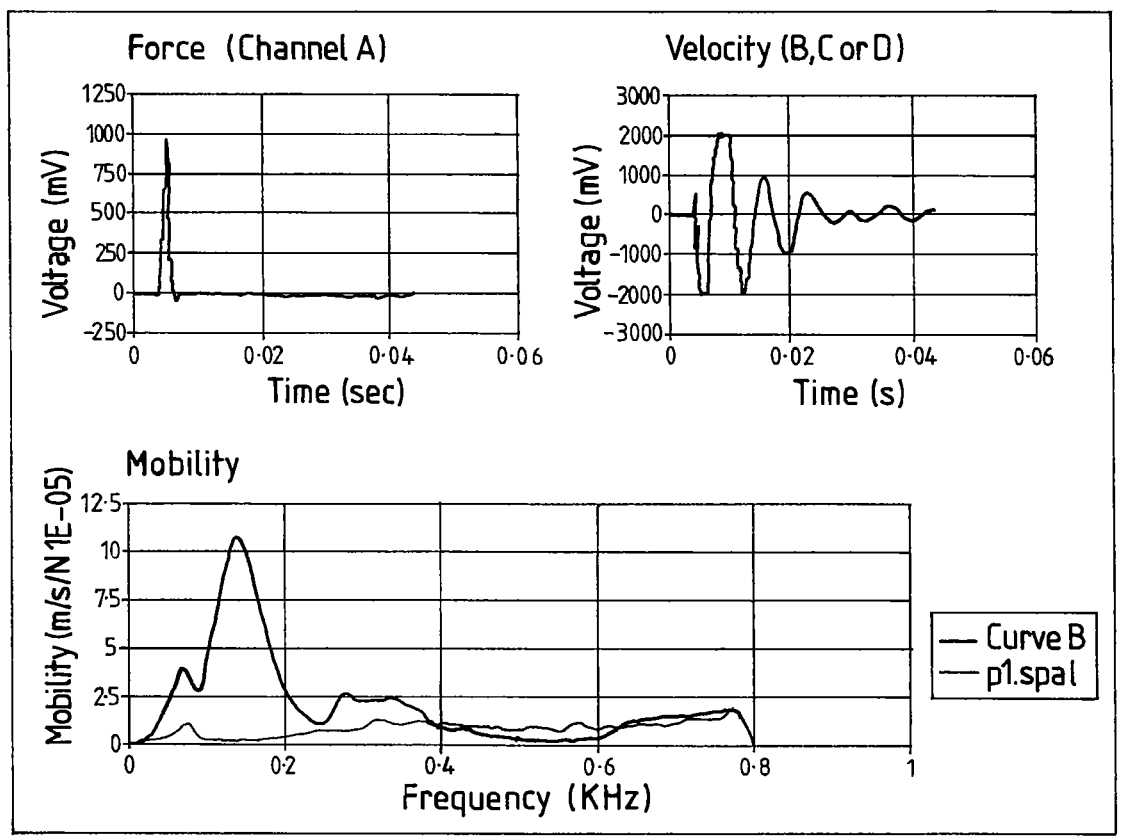
FIG. 16 shows the mobility curves (lower curve) for points 1 and 4 pre-repairs.

FIG. 16 shows the mobility curves (lower curve) for points 1 and 4 pre-repairs. Point 4 has a high average mobility and debond mobility ($3.7\times 10^{-5}$ and $10\times 10^{-5}$ m/s/N) which is characteristic of either a missing "hot face" or void at the interface. Point 1 on the other hand has a steady mobility in comparison and a low average mobility value ($0.64\times 10^{-5}$ m/s/N) which is indicative of a stable lining.

Figure 17:
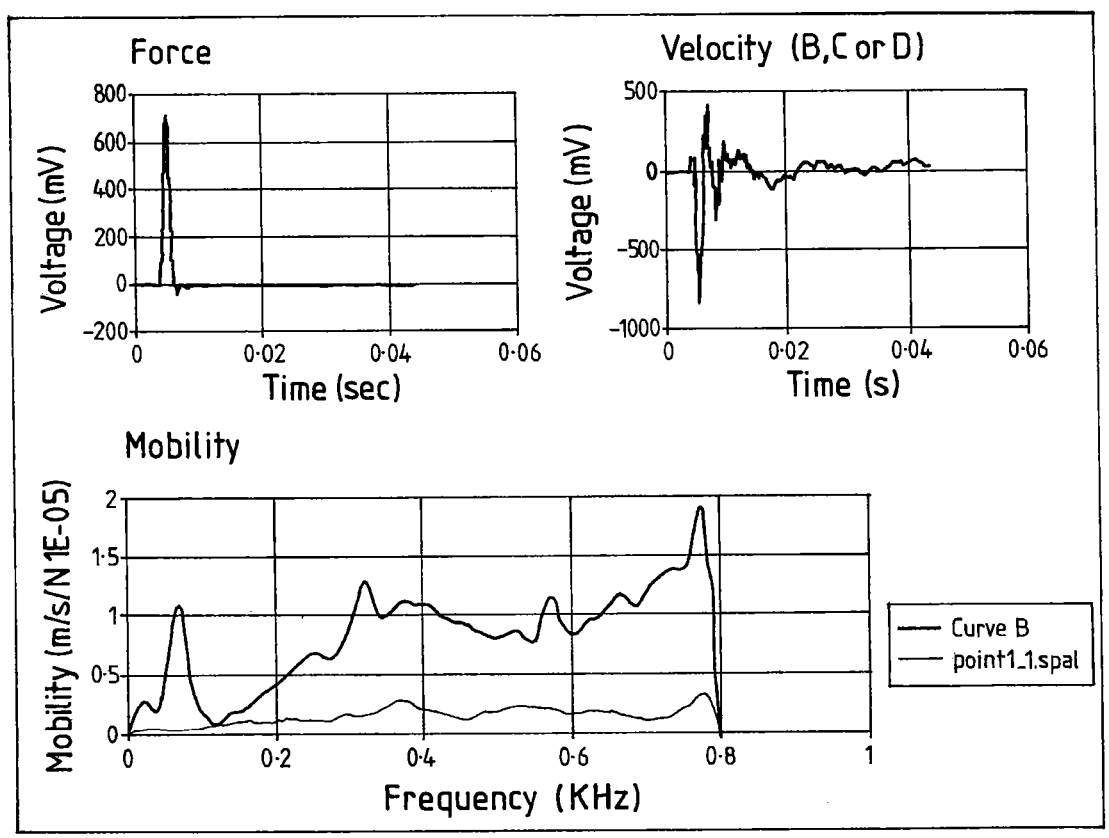
FIG. 17 shows the mobility trace for the cyclone roof at point 1 before and after repairs.

FIG. 17 shows the mobility trace for the cyclone roof at point 1 before and after repairs. The red line, pre-repair has an increasing mobility which is characteristic of debonding at the interface. The purple line, post-repair is very flat and the average mobility is very low. This is characteristic of a new refractory lining correctly installed with no voids or laminations.

Further testing was conducted during the course of a regular plant shutdown of a refractory lined cyclone in a cement plant. It was found that the refractory lined cyclone had a section of the "hot face" finding missing and other areas were found to be unstable.

Figure 18:
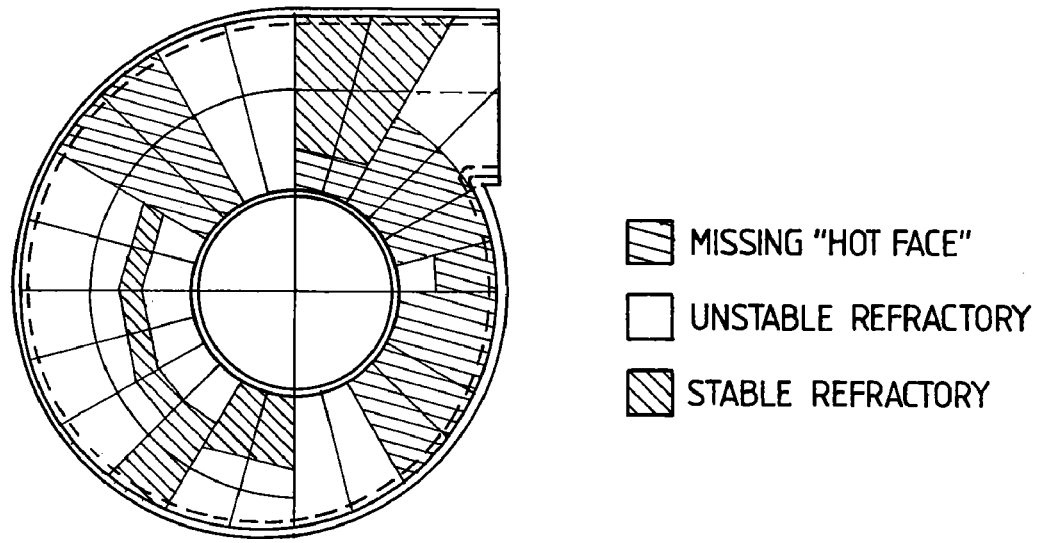
FIG. 18 shows a diagram of the cyclone roof showing the location of test points and damaged areas for a further test conducted in accordance with an embodiment of the present invention.

The damage lining was in the roof section of the pre-heater cyclone. The cyclone roof was constructed of three layers, being a dense "hot face" concrete layer, an insulation layer and then an outer steel shell. The refractory concrete is held in place with refractory anchors. FIG. 18 shows a diagram of the cyclone roof showing the location of test points and damaged areas.

The vessel roof was tested in accordance with the present invention. The approximate location of each test point is shown in FIG. 18. After the initial testing was carried out, it was found that the majority of the roof was unstable. The roof was secured with props and slowly demolished. Thus, the condition of the refractory lining was recorded during demolition, allowing for later assessment against the results obtained from the testing conducted in accordance with the present invention.

Figure 19:
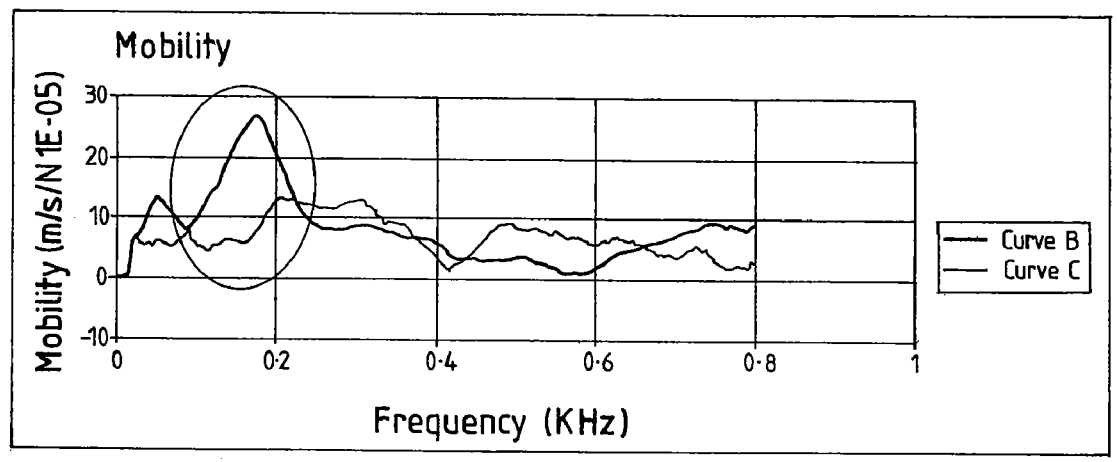
FIG. 19 shows the mobility curves (lower curve) for one point of the cyclone roof pre-repair for the test carried out on the cyclone roof shown in FIG. 19.

FIG. 19 shows the mobility curves (lower curve) for one point of the cyclone roof pre-repair. This point has a high peak mobility ($>20\times 10^{-5}$ m/sN) and a low peak frequency ($<0.2$ kHz), which is characteristics of either a missing "hot face" or a void at the interface. Visual inspection found missing hot face in this area.

Figure 20:
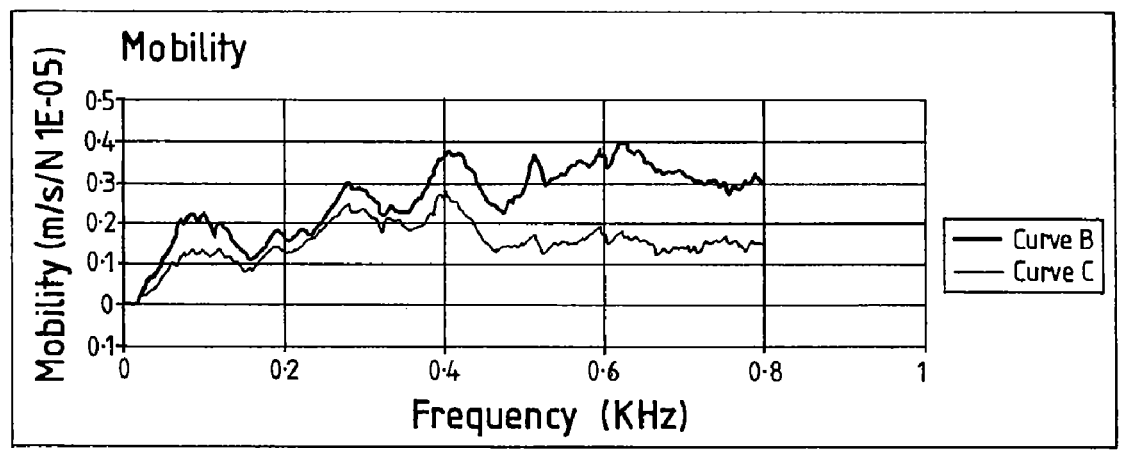
FIG. 20 shows the mobility trace for the cyclone roof at the point at which the measurements were made in respect of the output trace shown in FIG. 20, but after repairs had been made.

FIG. 20 shows the mobility trace for the cyclone roof at the point at which the measurements were made in respect of the output trace shown in FIG. 19, but after repairs had been made. The "as new" condition has a very low average mobility value ($<0.4\mathrm{x}^{-5}$ m/sN). This is characteristic of a new refractory lining correctly installed with no voids or laminations.

Persons skilled in the art will appreciate that the invention described above may be subject to improvements and modifications that will be apparent without departing from the spirit and scope of the invention described herein.

The invention claimed is:

1. A process for the non-destructive testing of a refractory lined process vessel comprising a vessel having an outer shell having a refractory lining positioned adjacent an inner wall of the outer shell, comprising the steps of:
    (a) striking an external wall of a process vessel internally lined with a refractory material with an impulse hammer;
    (b) measuring selected frequency characteristics of the refractory lined process vessel; and
    (c) analysing the measured frequency characteristics and determining the integrity of the internal lining of refractory material from said measured frequency characteristics by determining at least one of relative flexibility of the refractory lining, vibration modes of the refractory lining, relative density of the refractory lining, thickness of the refractory lining, delamination of the refractory lining, de-bonding within the refractory lining, and relative softness of the refractory lining.

2. A process according to claim 1 wherein the impulse hammer provides an impulse that consists of a nearly constant force applied over a broad frequency range.

3. A process according to claim 2 wherein the impulse hammer is provided with a tip capable of generating frequencies up to 2000 Hz.

4. A process according to claim 1 wherein the impulse hammer comprises an integral quartz force transducer for measuring the applied force on the striking end of the hammer.

5. A process according to claim 1 wherein the impulse hammer is a modally tuned impulse hammer.

6. A process according to claim 1 wherein the impulse hammer comprises inter-changeable softer and stiffer hammer tips to provide the desired frequency response in the process vessel.

7. A process according to claim 1 wherein the impulse hammer comprises extenders for increasing the hammer mass.

8. A process according to claim 1 wherein the response of the process vessel to the impact may be measured by one or more accelerometers.

9. A process according to claim 8 wherein the accelerometers are geophones.

10. A process according to claim 9 wherein the geophones have a single degree of freedom wherein the output of the geophone is generated by a coil moving though a magnetic field.

11. A process according to claim 8 wherein the output from the accelerometer and the force transducer of the impulse hammer are analysed across the frequency range for a variety of frequency characteristics in order to determine the integrity of the internal lining of refractory material.

12. A process according to claim 1 wherein the frequency characteristics of the refractory lined process vessel selected for determining the integrity of the internal lining of refractory material are selected from the group consisting of dynamic stiffness, average mobility, slope of average mobility, peak mobility, peak to average mobility ratio and combinations thereof.

13. A process according to claim 12 wherein the mobility of the refractory lined vessel is determined by the velocity of the response divided by the force applied by the impulse hammer.

14. A process according to claim 12 wherein the dynamic stiffness of the refractory lined process vessel is obtained from the mobility slope in the low frequency range.

15. A process for the non-destructive testing of a refractory lined process vessel comprising the steps of:
    (a) striking an external wall of a process vessel internally lined with a refractory material with an impulse hammer;
    (b) measuring selected frequency characteristics of the refractory lined process vessel wherein the frequency characteristics of the refractory lined process vessel selected for determining the integrity of the internal lining of refractory material are selected from the group consisting of dynamic stiffness, average mobility, slope of average mobility, peak mobility, peak to average mobility ratio and combinations thereof, wherein the dynamic stiffness of the refractory lined process vessel is obtained from the mobility slope in the low frequency range, and wherein the dynamic stiffness is determined from the mobility slope in the low frequency range between 0 and 200 Hz; and
    (c) analysing the measured frequency characteristics and determining the integrity of the internal lining of refractory material from said measured frequency characteristics.

16. A process for the non-destructive testing of a refractory lined process vessel comprising the steps of:
    (a) striking an external wall of a process vessel internally lined with a refractory material with an impulse hammer;
    (b) measuring selected frequency characteristics of the refractory lined process vessel wherein the frequency characteristics of the refractory lined process vessel selected for determining the integrity of the internal lining of refractory material are selected from the group consisting of dynamic stiffness, average mobility, slope of average mobility, peak mobility, peak to average mobility ratio and combinations thereof, wherein the dynamic stiffness of the refractory lined process vessel is obtained from the mobility slope in the low frequency range, and wherein the dynamic stiffness is determined from the force curve (slope) between 0 and 1000 Hz; and
    (c) analysing the measured frequency characteristics and determining the integrity of the internal lining of refractory material from said measured frequency characteristics.

17. An apparatus for the non-destructive testing of a refractory lined process vessel comprising a vessel having an outer shell having a refractory lining positioned adjacent an inner wall of the outer shell comprising:
    (a) an impulse hammer for striking an external wall of a process vessel internally lined with a refractory material;
    (b) one or more accelerometers for measuring selected frequency characteristics of the refractory lined process vessel; and
    (c) a computer for analysing the measured frequency characteristics and determining the integrity of the internal lining of refractory material from said measured frequency characteristics by analysing the measured frequency characteristics and determining at least one of relative flexibility of the refractory lining, vibration modes of the refractory lining, relative density of the refractory lining, thickness of the refractory lining, delamination of the refractory lining, de-bonding within the refractory lining, and relative softness of the refractory lining.

18. An apparatus according to claim 17 wherein the impulse hammer provides an impulse that consists of a nearly constant force applied over a broad frequency range.

19. An apparatus according to claim 18 wherein the impulse hammer is provided with a tip capable of generating frequencies up to 2000 Hz.

20. An apparatus according to claim 17 wherein the impulse hammer comprises an integral quartz force transducer for measuring the applied force on the striking end of the hammer.

21. An apparatus according to claim 17 wherein the impulse hammer is a modally tuned impulse hammer.

22. An apparatus according to claim 17 wherein the impulse hammer comprises inter-changeable softer and stiffer hammer tips to provide the desired frequency response in the process vessel.

23. An apparatus according to claim 17 wherein the impulse hammer comprises extenders for increasing the hammer mass.

24. An apparatus according to claim 17 wherein the accelerometers are geophones.

25. An apparatus according to claim 24 wherein the geophones have a single degree of freedom wherein the output of the geophone is generated by a coil moving though a magnetic field.

26. An apparatus according to claim 17 wherein the output from the accelerometer and the force transducer of the impulse hammer are analysed across the frequency range for a variety of frequency characteristics in order to determine the integrity of the internal lining of refractory material.

27. An apparatus according to claim 17 wherein the frequency characteristics of the refractory lined process vessel selected for determining the integrity of the internal lining of refractory material are selected from the group consisting of dynamic stiffness, average mobility, slope of average mobility, peak to average mobility ratio and combinations thereof.

28. An apparatus according to claim 17 wherein computer determines the mobility of the refractory lined pressure vessel is determined by the velocity of the response divided by the force applied by the impulse hammer.

29. An apparatus according to claim 17 wherein computer determines the dynamic stiffness of the refractory lined process vessel is obtained from the mobility slope in the low frequency range.

30. An apparatus for the non-destructive testing of a refractory lined process vessel comprising the steps of:
(a) an impulse hammer for striking an external wall of a process vessel internally lined with a refractory material;
(b) one or more accelerometers for measuring selected frequency characteristics of the refractory lined process vessel;
(c) a computer for analysing the measured frequency characteristics and determining the integrity of the internal lining of refractory material from said measured frequency characteristics; and
(d) wherein the computer determines the dynamic stiffness of the refractory lined process vessel is obtained from the mobility slope in the low frequency range between 0 and 200 Hz.

31. An apparatus for the non-destructive testing of a refractory lined process vessel comprising the steps of:
(a) an impulse hammer for striking an external wall of a process vessel internally lined with a refractory material;
(b) one or more accelerometers for measuring selected frequency characteristics of the refractory lined process vessel;
(c) a computer for analysing the measured frequency characteristics and determining the integrity of the internal lining of refractory material from said measured frequency characteristics; and
(d) wherein the computer determines the dynamic stiffness of the refractory lined process vessel is obtained from the force curve (slope) between 0 and 1000 Hz.

32. A process according to claim 1 wherein the selected frequency characteristics include vibration amplitude.

* * * * *